(12) United States Patent
Postlethwaite et al.

(10) Patent No.: US 7,718,765 B2
(45) Date of Patent: May 18, 2010

(54) METHODS OF TREATING FIBROSING DISEASES BY INDUCTION OF IMMUNE TOLERANCE

(75) Inventors: Arnold E. Postlethwaite, Eads, TN (US); Andrew H. Kang, Memphis, TN (US)

(73) Assignee: The University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 11/600,525

(22) Filed: Nov. 16, 2006

(65) Prior Publication Data

US 2007/0142286 A1 Jun. 21, 2007

Related U.S. Application Data

(60) Provisional application No. 60/737,194, filed on Nov. 16, 2005.

(51) Int. Cl.
*C07K 14/00* (2006.01)
*A61K 38/00* (2006.01)

(52) U.S. Cl. .......... 530/300; 514/2; 424/184.1
(58) Field of Classification Search .......... None
See application file for complete search history.

(56) References Cited

U.S. PATENT DOCUMENTS

| 5,962,025 | A | 10/1999 | Carbone et al. |
|---|---|---|---|
| 2003/0060438 | A1 | 3/2003 | Henry et al. |
| 2003/0148983 | A1 | 8/2003 | Fontoura et al. |
| 2005/0197283 | A1 | 9/2005 | Harats et al. |

*Primary Examiner*—Anand U Desai
(74) *Attorney, Agent, or Firm*—Patton Boggs LLP

(57) ABSTRACT

The present invention has demonstrated for the first time that orally administered type I collagen (CI) induced tolerance to CI in patients suffering from systemic sclerosis (SSc) and ameliorated clinical manifestations of the disease. Accordingly, the present invention provides methods of treating a fibrosing disease by oral administration of a tissue protein, for example, collagen, derived from the tissue undergoing fibrosis.

6 Claims, 4 Drawing Sheets

METHODS OF TREATING FIBROSING DISEASES BY INDUCTION OF IMMUNE TOLERANCE

CROSS REFERENCE TO RELATED APPLICATION

This application claims priority from U.S. Provisional Application No. 60/737,194, filed on Nov. 16, 2005.

FIELD OF THE INVENTION

This invention generally relates to treatment of fibrosing diseases. In particular, the present invention relates to treatment of fibrosing diseases by induction of immune tolerance.

BACKGROUND OF THE INVENTION

Acquired fibrosing diseases in humans have several common features. Tissue fibrosis is preceded by injury to and/or inflammation of the normal tissue. Infiltrations of the tissue by T cells and monocytes are present in the early phases of fibrosis development.

Systemic sclerosis (SSc, scleroderma) is a prototypic systemic fibrosing disease associated with increased accumulation of collagen type I, III, IV, VI, VII, XVI, XVIII. Cellular and/or humoral immunity to types I, III and IV have been described in patients with SSc. The disease most characteristically involves the skin which becomes thick and tightly bound to underlying structures. The internal organs commonly involved are gastrointestinal tract, lungs, kidneys, and heart.

T lymphocytes via synthesis of cytokines of different types can modulate the functions of fibroblasts and monocytes/macrophages as well as a variety of other target cells. With regards to fibrosis, the production of fibrogenic cytokines by T cells such as IL-4, TGF-$\beta$1 and $\beta$2, can directly stimulate synthesis of collagen by fibroblasts in culture. T cells by secreting interferon (IFN) gamma can activate macrophages, which in turn can synthesize several fibrogenic cytokines including platelet derived growth factor, TGF-$\beta$1 and $\beta$2 which in turn can stimulate fibroblasts to increase synthesis of collagen.

SUMMARY OF THE INVENTION

The present invention provides methods for treating a fibrosing disease by oral administration of a tissue protein derived from the tissue undergoing fibrosis.

The fibrosing diseases that can be treated in accordance with the present invention include, but are not limited to, scleroderma (SSc), skin fibrosis, liver cirrhosis, renal fibrosis, lung fibrosis, heart fibrosis, gastrointestinal fibrosis and vascular fibrosis.

In one embodiment, the present methods are utilized to treat a patient suffering from a fibrosing disease for at least 3 years, preferably, for at least 5 years.

In another embodiment, a fibrosing disease is treated by oral administration of a collagen derived from the tissue(s) undergoing fibrosis. Depending upon the tissue type, different types of collagen may be employed in the treatment. Collagen can be prepared from the tissue undergoing fibrosis in a human patient, or from the corresponding tissue of an animal, such as an avian species or a mammal. Alternatively, chemically synthesized or recombinantly produced collagen can be employed. A fragment or a mixture of fragments of collagen can also be employed according to the present invention.

In a preferred embodiment, collagen or fragments of collagen are provided to a patient by oral administration at about 500 µg/day for about 12 months.

DETAILED DESCRIPTION OF THE INVENTION

Figure 1:
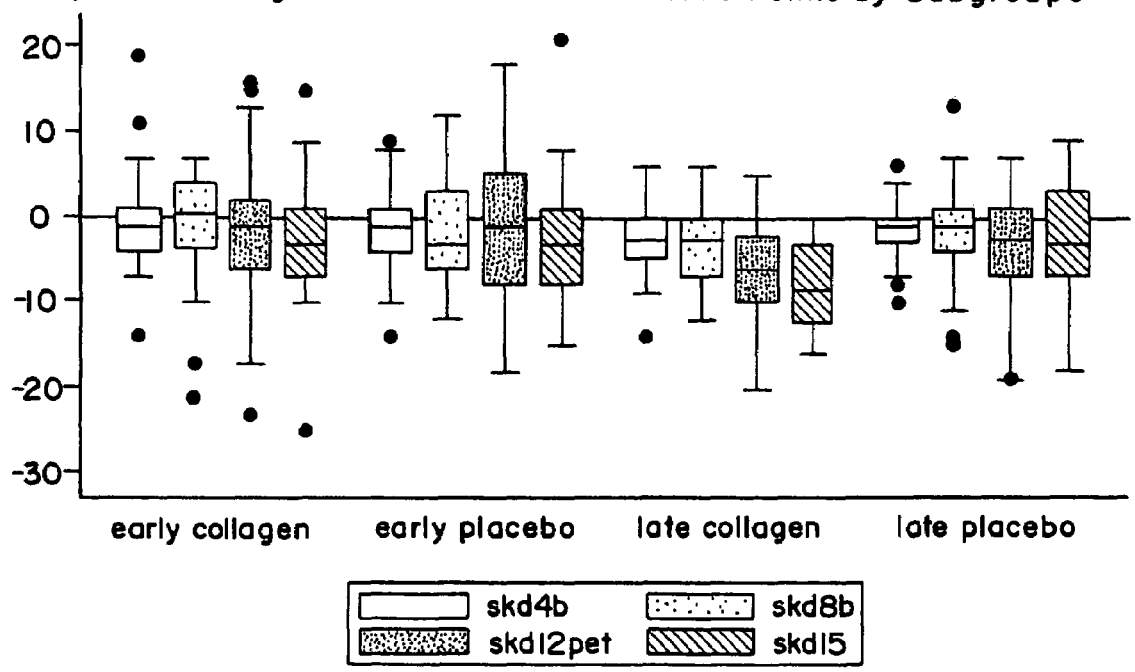
FIG. 1 depicts boxplots of changes in MRSS at different time points in different SSc patient subgroups.

The present invention has demonstrated for the first time that orally administered type I collagen (CI) induced tolerance to CI in patients suffering from systemic sclerosis (SSc) and ameliorated clinical manifestations of the disease.

SSc is a prototypic systemic fibrosing disease associated with an increased accumulation of extracellular matrix proteins such as collagen. Without intending to be bound by any particular theory, it is believed that oral administration of a tissue protein (such as collagen) present at the tissue site undergoing fibrosis where T cells are being activated by various stimuli, can down-regulate T cells. Consequently, T cells are inhibited from secreting fibrogenic cytokines and cytokines that activate monocytes/macrophages, which cytokines would otherwise stimulate fibroblasts at the tissue site to produce extracellular matrix proteins such as collagen.

Accordingly, the present invention provides methods of treating a fibrosing disease by oral administration of a tissue protein derived from the tissue undergoing fibrosis.

The fibrosing diseases that can be treated with the present methods include, but are not limited to, SSc, skin fibrosis, liver cirrhosis, renal fibrosis, lung fibrosis, heart fibrosis (as occurs, for example, in congestive heart failure), gastrointestinal fibrosis and vascular fibrosis as occurs in atherosclerosis. The methods of the present invention can treat these fibrosing diseases regardless of the cause of the disease.

In a specific embodiment, the present methods are utilized to treat a patient suffering from a fibrosing disease for at least 3 years, preferably, for at least 5 years.

According to the present invention, a fibrosing disease can be treated by oral administration of a collagen derived from the tissue(s) undergoing fibrosis. For example, SSc is known to associate with excessive accumulation of type I collagen, and therefore type I collagen or a fragment thereof is orally administered to patients suffering SSc. Liver cirrhosis, lung fibrosis, and interstitial collagen disease are associated with increased accumulation of type I, III, and V collagen, respectively. Therefore, type I, III and V collagens or a fragment(s) thereof are orally administered to patients suffering from liver cirrhosis, lung fibrosis, and interstitial collagen disease, respectively. Small synthetic peptides from collagen may also induce tolerance when given nasally, for example, by nose drops or nose spray, or inhaled by aerosolization.

Collagen can be prepared and extracted from the tissue undergoing fibrosis in a human patient, or from the corresponding tissue(s) of an animal, such as an avian species (e.g., domestic chickens) or a mammal (e.g., bovine or porcine). Alternatively, chemically synthesized or recombinantly produced collagen can be employed. Moreover, a fragment or a mixture of fragments of collagen can also be employed according to the present invention. For example, peptides derived by cleavage of type I collagen with CNBr can be employed in treating a patient suffering from SSc.

Collagen or fragments of collagen can be provided to a patient by oral administration at about 200-1000 µg/day, preferably about 400-600 µg/day, and more preferably at about 500 µg/day. The treatment can continue for at least six months, preferably 12 months or longer, or until the clinical manifestations of the disease are reduced or ameliorated.

The present invention is further illustrated by the following examples.

Example 1

To determine whether orally administered bovine type I collagen (CI) at doses of 500 µg/day ameliorates clinical manifestations of systemic sclerosis (SSc), a multicenter double blind placebo-controlled study was conducted.

Patients were screened based on the following criteria in order to be included in the study:
Male or female of at least 18 years old;
Clinically diagnosed to have diffuse SSc (by ACR criteria 1980) for 3 years or less (early phase), or between 4 and 10 years (late phase);
Stable skin involvement by history or physical examination during the 6 months preceding enrollment; and
Stable modified Rodnan skin score (MRSS) 1 month preceding enrollment: stable MRSS≧16 at screening and stable MRSS at randomization (baseline) as follows:

| MRSS at screen | Allowable MRSS at randomization (baseline) |
|---|---|
| 16 | up to 20 |
| 17-20 | 16-24 |
| 21-25 | ±4 |
| 26-30 | ±5 |
| ≧31 | ±7 |

168 patients who met the foregoing criteria were stratified and randomized to receive daily placebo [2 ml 0.1M acetic acid (HAc)] or 500 µg bovine CI for 12 months. MRSS was measured as a primary clinical outcome variable at baseline and after 4, 8, 12, and 15 months. Scleroderma Health Assessment Questionnaire (SHAQ), Short Form 36 (SF-36) questionnaire, Physician's Global Assessment, Patient's Global Assessment, blood pressure, weight and serum creatinine were determined as secondary clinical outcome measures at baseline and after 4, 8, 12, and 15 months. Patients had FVC and DLCO measured no earlier than 5 weeks before baseline, and 12 months as secondary clinical outcome parameters. A prescreening visit was also required for patients taking any exclusionary drugs/treatments.

FIG. 1 summarizes the changes in MRSS at month 4 (blue), month 8 (red), month 12 (green) and month 15 (orange) from baseline and broken down by the four subgroups. Each boxplot describes the distribution of the change in MRSS in each group and at each time point; the upper edge is the 75% percentile; the lower edge is the 25%; and the line inside the box represents the median change in MRSS. Outlying values are presented by whiskers from the box.

The results indicate that there was no statistical difference in the mean change between the CI-treated group and the placebo group at 12 month. Similar conclusions applied to the other clinical and laboratory parameters as well (see Table 1 and Table 2). However, at 15 month, there was a very noticeable change in MRSS: 7.9 in the late phase patients treated with CI (the "late collagen" group) and 2.9 in the late phase patients in the placebo ("late placebo") group. As shown in FIG. 1, at 15 month, the median value in the orange box for the late phase patient group treated with collagen is clearly substantially lower than the median values in the other orange boxes, and in fact is also the lowest for all the boxes. This means that patients in the late phase subgroup treated with CI experienced the greatest improvement in MRSS. The p-value of the mean difference in MRSS between treatment groups for late phase patients is 0.0063; all other tests are not significant at the 0.05 level. It is noted that the variable MRSS by itself is not normally distributed, but the change in MRSS at 12 or 15 month from baseline is normally distributed. Hence, the p-value was obtained from the t-test. A non-parametric test was also used to ascertain change in MRSS between the treated and placebo group, namely the rank-sum test, and the p-value was similar.

Figure 2:
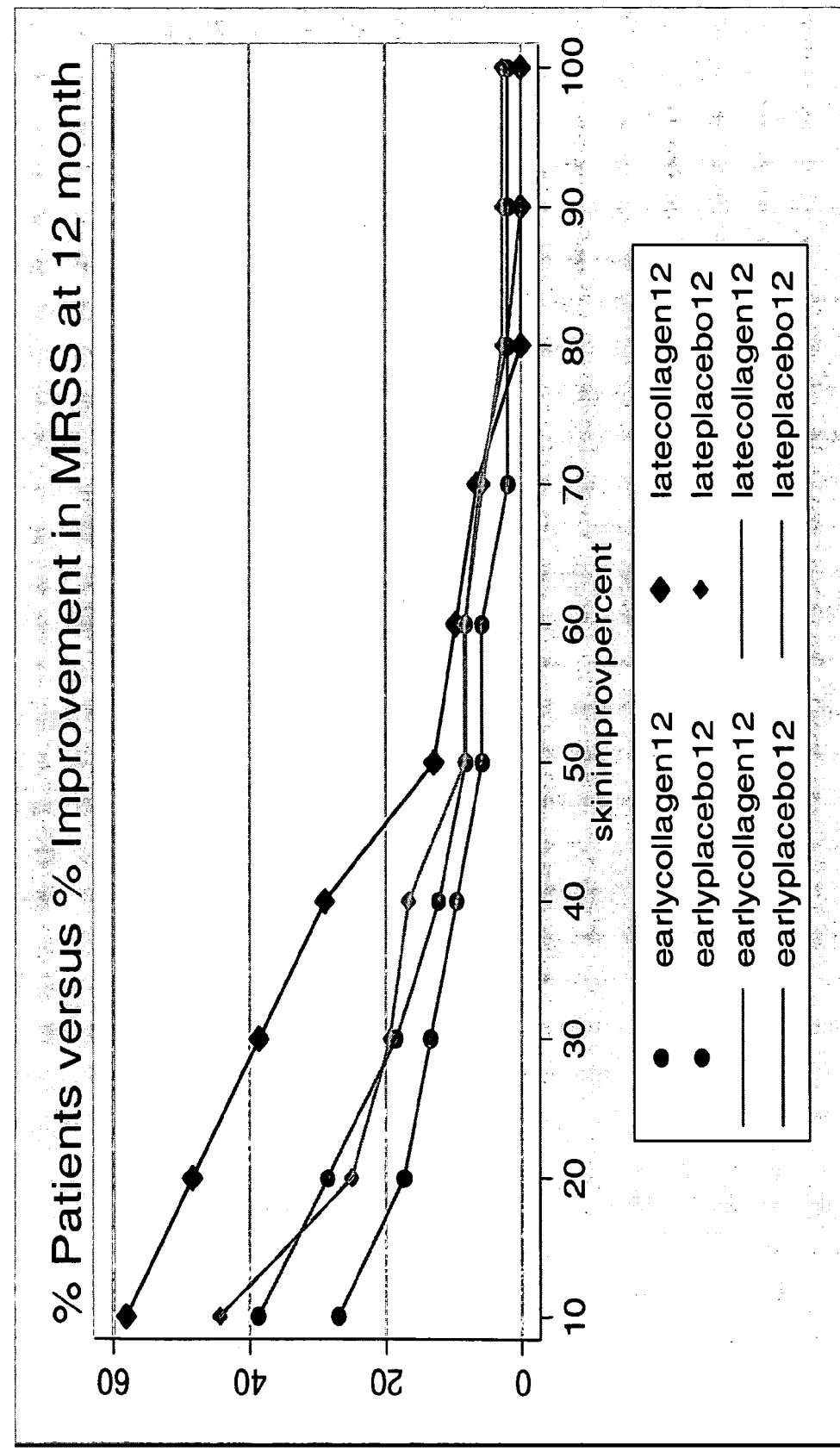
FIG. 2 correlates percentages of SSc patients versus percentages of improvement in MRSS at 12 month.
Figure 3:
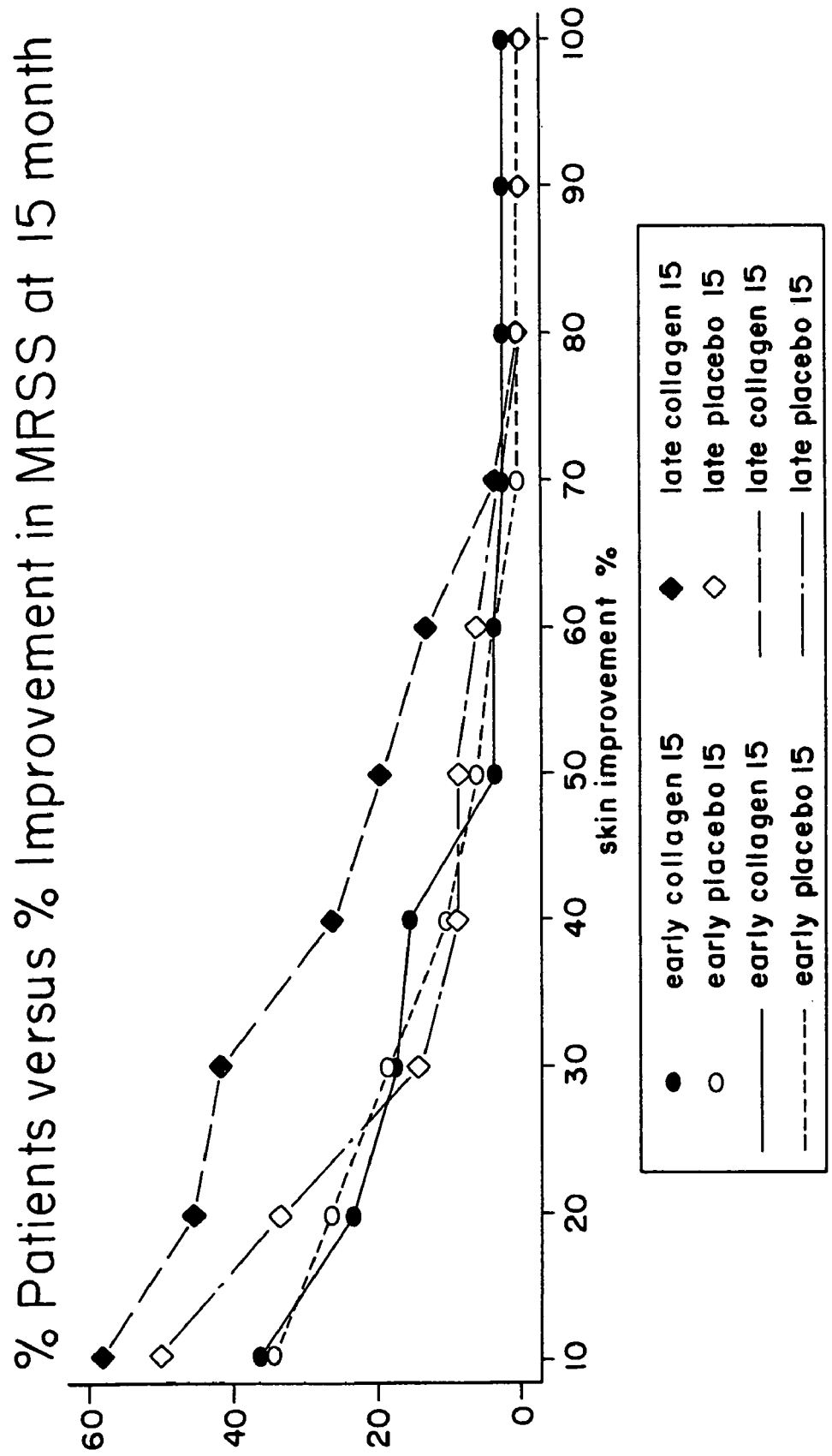
FIG. 3 correlates percentages of SSc patients versus percentages of improvement in MRSS at 15 month.

When changes in MRSS were dichotomized and the percentage of patients who had skin improvement in MRSS was determined, two graphs were obtained (FIG. 2 and FIG. 3). Each graph plots the percentage of the cohort in each of the four subgroups who experienced different degrees of improvement in MRSS. For instance, in the first plot, almost 50% of patients in the late collagen group had a reduction of 20% in MRSS at 12 month. In contrast, only about 19% experienced a similar improvement in the early collagen group. Both plots clearly show that the late phase patients benefited most from the collagen treatment compared with the other subgroups. Among the collagen group, the Chi-squared test confirmed that at 15 months, a significantly higher proportion of the late phase patients had at least a 25% improvement in MRSS compared with the early phase patients.

In sum, the foregoing study shows that orally administered bovine CI at 500 µg/day for 12 months was found to significantly decrease the MRSS at Month 15 of the study in patients with disease duration of ≧4 to 10 years, indicating a delayed effect of the oral collagen treatment on skin fibrosis. There were no discernable effects of oral CI in this study on PFTs or HAQ, and no adverse events that could be attributable to the CI treatment. The delayed effect of the oral collagen treatment is consistent with the notion that it takes some time for fibroblasts to "wind down" once the T cell stimuli are neutralized. These results also suggest that T cells provide a major source of fibrogenic signals only in late phase patients.

Example 2

This Example describes experiments conducted to determine whether the oral CI treatment at 500 µg/day induced tolerance to CI in the patients enrolled in the study described in Example 1.

Figure 4:
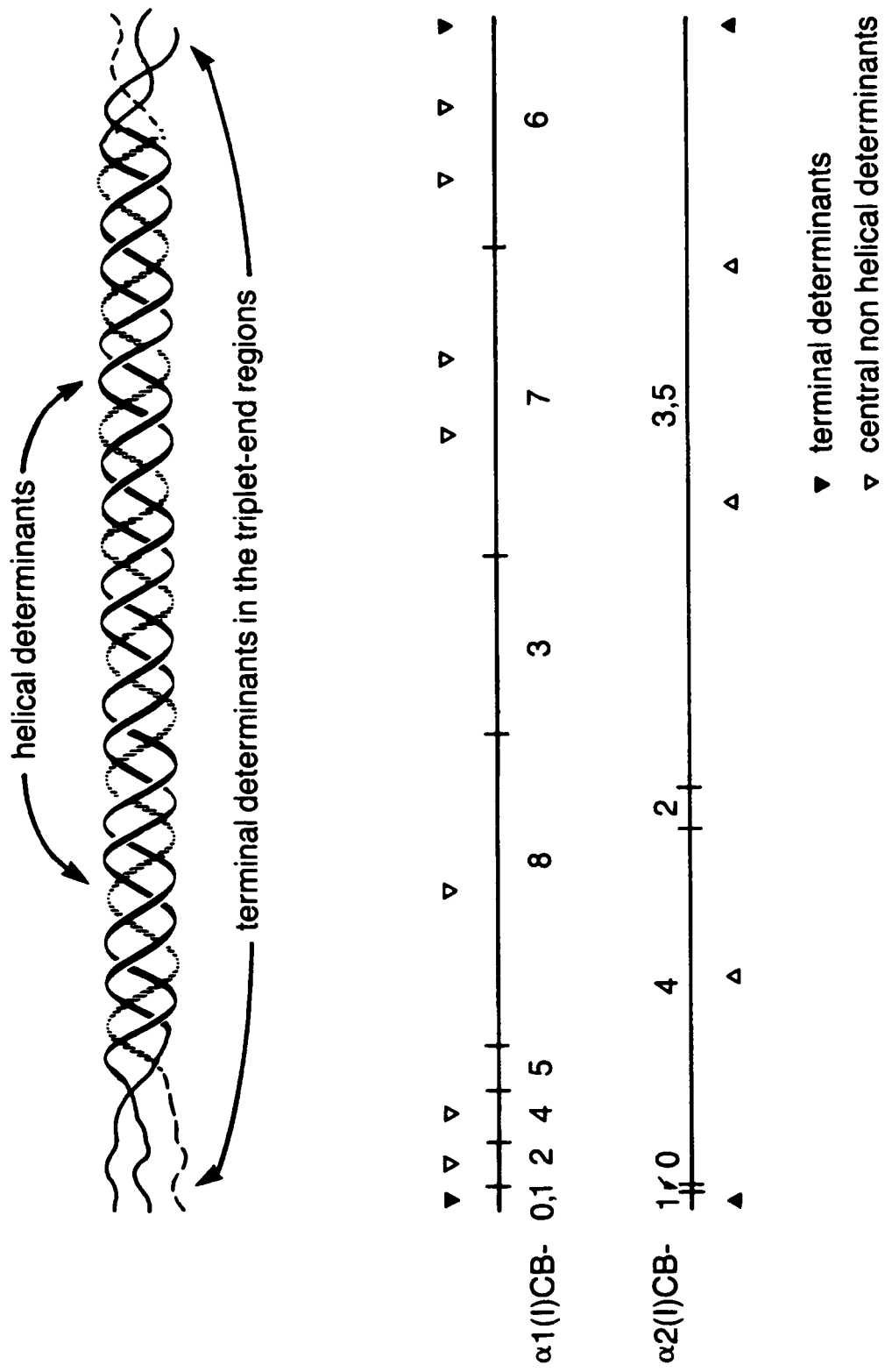
FIG. 4 is a graphical representation of $\alpha$1(I) and $\alpha$2(I) cleaved with cyanogen bromide (CNBr). The solid triangles represent the location of terminal determinants, and the hollow triangles represent the location of central non helical determinants. CNBr cleavage of $\alpha$1(I) yields eight CB fragments: CB0, CB1, CB2, CB4, CB5, CB8, CB3, CB7 and CB6. GNBr cleavage of $\alpha$2(I) yields six GB fragments: CB1, CB0, CB4, CB2, CB3 and CB5. The amino acid residues of each CB peptide are shown in Table III.

Serum and PBMC were obtained from patients before and after the 12 month treatment with oral bovine CI, or at dropout greater than or equal to 3 months to less than or equal to 11 months. The PBMC were cultured with or without bovine α1(I) chain, bovine α2(I) chain, native bovine CI, or CB (CNBr) peptides of α1(I) or α2(I). CB peptides were isolated by cleavage of bovine or human α1(I) and α2(I) with CNBr (illustrated in FIG. 4 and Table 3) and purification by ion exchange chromatography. Purified CB peptides of α1(I) and α2(I) as well as unseparated CB peptides of α1(I) and α2(I) were used in the culture of PBMC from SSc patients at baseline before administration of CI or placebo and at 12 months. The PBMC supernatants were analyzed by ELISA for IFNγ and IL-10, at 0 and 12 months. Decreases in IFNγ or increases in IL-10 production by a chain-stimulated PBMC after oral CI were determined as the primary immunology outcome variable. The results are summarized in Tables 4-9.

As can be seen from Tables 5-6, significant decreases were observed in the production of IFNγ by PMBC to α1(I) CB peptide mixture and to α2(I) CB7 in the Total and Early Disease Phase patient population treated with oral CI for 12 months. Additionally, significant increases were observed in the IL-10 production by PBMC cultured with human α2(I) and α1(I) CB7 in the Total and Late Phase patient population (Tables 7-8). These results suggest that oral Bovine CI is potentially efficacious in treating patients with diffuse SSc of ≧4 years duration apparently by modulating TH1/TH2 production. Upregulation of antigen-specific IL-10 production suggests that tolerance was induced to CI in LD patients.

For the total SSc population, there were inverse correlations between disease duration and IL-10 production by the following: α1(I) CB3 ($p=-0.0059$. $N=153$); α1(I) CB7 ($p=-0.0335$, $N=150$); human α1(I) ($p=-0.0166$, $N=152$); and α2(I) CB Mixture ($p=-0.0032$. $N=154$).

For Early patients, there was an inverse correlation between MRSS and IFNγ production to α2(l) CB2 ($p=-0.026$, $N=94$).

For the total SSc population, there was an inverse correlation between SF-36 and IFNγ production to α1(I) CB4 ($p=-0.0448$, $N=143$). For Late patients, there were inverse correlations between SF-36 and IFNγ production to α1(I) CB4 and PHA ($p=-0.0364$, $N=57$; $p=-0.028$, $N=58$, respectively).

For the total diffuse SSc population, there were direct correlations between FVC and IL-10 production by PBMC cultured with α1(1) CB4 and human α2(I) ($p=0.0122$, $N=152$; $p=0.0072$, $N=94$, respectively).

For Early patients, there was a direct correlation between FVC and IL-10 production to human α2(1) ($p=0.0062$, $N=94$).

For Early Patients, there was an inverse correlation between FEV1 and IL-10 production to α2(1) CB4 and α1(I) CB Mixture ($p=-0.0067$, $N=92$; $p=-0.0041$, $N=94$, respectively). For the total diffuse SSc population, there was an inverse correlation between FEV1 and IL-10 production to α1(I) CB Mixture ($p=0.0241$, $N=154$).

In the Early patients, there was a direct correlation between DLCO and IFNγ production to α1(I) CB7 ($p=0.0367$, $N=90$). In the Late patients, there was a direct correlation between DLCO and IFNγ production to α2(1) CB2 ($p=0.0383$, $N=59$).

In sum, the immune response studies conducted by culturing PBMC from the patients with CI and CI-derived peptides showed that, in general, greater IFNγ and IL-10 production by cultured PBMC occurred in patients with Early Phase diseases (<4 years duration). IFNγ production to the antigen *C. albicans* was absent in both early and late phase patients, suggesting impaired Th1 responsiveness to common environmental antigens. Native Bovine CI elicited significant increases in IFNγ and IL-10 production in both early and late phase patients. Specific CI CB peptides that failed to elicit IFNγ or IL-10 production in late phase patients included α1(I) CB2, 4, 5 and 7, and α2(I) CB2, 3 and 3-5. The strongest consistent IFNγ and IL-10 response in both early and late phase patients was observed with α1(I) CB8, α1(I) CB6, α2(I) CB4, indicating these portions of α1(I) and α2(I) contain epitopes that elicit T cell responses throughout the duration of the disease in the majority of patients with diffuse SSc. Correlations between specific PBMC IFNγ or IL-10 responses to CI and CI derived peptides suggest that subsets of patients might exist in which the particular cytokine response to specific CI epitopes might influence disease expression.

TABLE 1

Scleroderma HAQ Changes Between Baseline and Months 12 and 15

| | Month 12 | | Month 15 | |
|---|---|---|---|---|
| | (n) Mean ± SEM | p value | (n) Mean ± SEM | p value |
| Total Placebo | (56) −0.028 ± 0.061 | NS | (56) 0.0222 ± 0.061 | NS |
| Total CI | (46) 0.114 ± 0.078 | | (39) 0.674 ± 0.084 | |
| Early Placebo | (27) −0.022 ± 0.093 | NS | (28) 0.009 ± 0.098 | NS |
| Early CI | (30) 0.125 ± 0.097 | | (24) −0.010 ± 0.096 | |
| Late Placebo | (30) −0.0337 ± 0.081 | NS | (28) 0.054 ± 0.076 | NS |
| Late CI | (16) 0.094 ± 0.134 | | (15) 0.191 ± 0.155 | |

TABLE 2

PFT Changes Between Baseline and Month 12

| | (n) FEV$_1$ | | (n) FVC | | (n) DL$_{CO}$ | |
|---|---|---|---|---|---|---|
| | Mean ± SEM | p value | Mean ± SEM | p value | Mean ± SEM | p value |
| Total Placebo | (61) −0.46 ± 1.67 | NS | (60) −0.68 ± 1.20 | NS | (59) −2.66 ± 2.23 | NS |
| Total CI | (47) −2.02 ± 3.05 | | (40) −4.54 ± 2.41 | | (47) −5.74 ± 2.58 | |
| Early Placebo | (30) −0.17 ± 3.18 | NS | (29) −0.83 ± 2.11 | NS | (29) −1.76 ± 3.21 | NS |
| Early CI | (30) −2.07 ± 4.74 | | (31) −5.42 ± 3.66 | | (31) −4.81 ± 3.77 | |
| Late Placebo | (31) −0.74 ± 1.23 | NS | (31) −0.55 ± 1.25 | NS | (30) −3.53 ± 2.59 | NS |
| Late CI | (17) −1.94 ± 1.45 | | (17) −2.94 ± 1.42 | | (16) −7.51 ± 3.99 | |

TABLE III

Amino Acid Residues Contained in Human CI CB Peptides

Human α1(I) CB Peptides

| Residue # | CB Peptide | Number of Amino Acid Residues |
|---|---|---|
| 1-3 | CB1 | 3 |
| 4-39 | CB2 | 36 |
| 40-86 | CB4 | 47 |
| 87-123 | CB5 | 36 |
| 124-402 | CB8 | 279 |
| 403-551 | CB3 | 149 |
| 552-842 | CB7 | 291 |
| 843-1014 | CB6 | 172 |

Human α2(I) CB Peptides

| Residue # | CB Peptide | Number of Amino Acid Residues |
|---|---|---|
| 1-3 | CB0 | 3 |
| 4-6 | CB1 | 3 |
| 7-327 | CB4 | 321 |
| 328-357 | CB2 | 30 |
| 358-695 | CB3 | 338 |
| 696-1014 | CB5 | 319 |

TABLE 4

IFNγ Production at Baseline and 12 Months

| | (n) PBS | (n) PHA | (n) Cand | (n) H α1 (I) | (n) H α2 (I) | BCI |
|---|---|---|---|---|---|---|
| Total Placebo | | | | | | |
| Baseline | (58) 389 ± 71 | (57) 2837 ± 190 | (50) 497 ± 113 | (55) 876 ± 139 | (55) 766 ± 132 | (57) 728 ± 116 |
| Month 12 | (46) 734 ± 111 | | (58) 671 ± 133 | (54) 769 ± 107 | (54) 685 ± 112 | (58) 970 ± 150 |
| Total CI | | | | | | |
| Baseline | (46) 407 ± 71 | (46) 2844 ± 233 | (38) 840 ± 194 | (44) 950 ± 176 | (44) 848 ± 163 | (46) 638 ± 118 |
| Month 12 | (46) 508 ± 79 | (46) 2178 ± | (45) 539 ± 140 | (45) 767 ± 113 | (45) 749 ± 103 | (46) 655 ± 126 |
| p value | 0.184 | | 0.046 | 0.888 | 0.544 | 0.293 |
| Early Placebo | | | | | | |
| Baseline | (28) 239 ± 57 | (27) 2955 ± 250 | (24) 339 ± 124 | (26) 627 ± 147 | (26) 516 ± 119 | (27) 714 ± 187 |
| Month 12 | (28) 648 ± 131 | | (28) 487 ± 115 | (26) 571 ± 82 | (26) 536 ± 92 | (28) 795 ± 194 |
| Early CI | | | | | | |
| Baseline | (30) 324 ± 81 | (30) 2982 ± 28 | (25) 989 ± 283 | (29) 1190 ± 253 | (29) 1042 ± 236 | (30) 672 ± 166 |
| Month 12 | (30) 544 ± 108 | (30) 2062 ± 291 | (29) 627 ± 211 | (29) 692 ± 122 | (29) 684 ± 116 | (30) 709 ± 177 |
| p value | 0.371 | | 0.246 | | | 0.798 |
| Late Placebo | | | | | | |
| Baseline | (30) 528 ± 123 | (30) 2731 ± 286 | (26) 644 ± 183 | (29) 1099 ± 222 | (29) 990 ± 220 | (30) 740 ± 146 |
| Month 12 | (30) 815 ± 178 | | (30) 842 ± 231 | | (28) 823 ± 196 | (28) 795 ± 195 |
| Late CI | | | | | | |
| Baseline | (16) 563 ± 133 | (16) 2585 ± 352 | (13) 554 ± 150 | (15) 486 ± 102 | (15) 473 ± 103 | (16) 573 ± 143 |
| Month 12 | (16) 439 ± 103 | (16) 2397 ± | (16) 378 ± 90 | (16) 902 ± 230 | (16) 866 ± 203 | (16) 554 ± 147 |
| p value | 0.153 | | 0.245 | 0.106 | 0.061 | 0.240 |

TABLE 5

IFNγ Production by SSc PBMC Cultured with Bovine α1(I) CB Peptides at Baseline and 12 Months

α1(I) CB Peptides

| | (n) CB Mix | (n) CB2 | (n) CB4 | (n) CB5 | (n) CB8 | (n) CB3 | (n) CB7 | (n) CB6 |
|---|---|---|---|---|---|---|---|---|
| Total Placebo | | | | | | | | |
| Baseline | (58) 812 ± 160 | (56) 640 ± 97 | (56) 777 ± 159 | (56) 611 ± 126 | (56) 872 ± 147 | (57) 955 ± 161 | (55) 651 ± 121 | (55) 856 ± 151 |
| Month 12 | (57) 898 ± 138 | (55) 743± 122 | (55) 814 ± | (56) 750 ± 123 | (57) 832 ± 103 | (55) 1209 ± 172 | (57) 822 ± 116 | (56) 1044 ± 142 |
| Total CI | | | | | | | | |
| Baseline | (45) 1006 ± 173 | (45) 620 ± 142 | (46) 760 ± 171 | (46) 856 ± 183 | (46) 986 ± 167 | (46) 963 ± 183 | (46) 783 ± 135 | (46) 1001 ± 187 |
| Month 12 | (45) 683 ± 114 | (46) 457 ± 80 | (46) 862 ± 173 | (46) 713 ± 125 | (46) 808 ± 144 | (46) 943 ± 179 | (46) 591 ± 97 | (46) 1004 ± 176 |
| p value | 0.260 | | 0.565 | 0.464 | 0.156 | 0.793 | 0.034 | 0.294 |

TABLE 5-continued

IFNγ Production by SSc PBMC Cultured with Bovine α1(I) CB Peptides at Baseline and 12 Months α1(I) CB Peptides

| | (n) CB Mix | (n) CB2 | (n) CB4 | (n) CB5 | (n) CB8 | (n) CB3 | (n) CB7 | (n) CB6 |
|---|---|---|---|---|---|---|---|---|
| Early Placebo | | | | | | | | |
| Baseline | (28) 769 ± 240 | (27) 656 ± 123 | (27) 643 ± 162 | (27) 534 ± 152 | (26) 659 ± 197 | (28) 876 ± 207 | (26) 492 ± 151 | (26) 648 ± 190 |
| Month 12 | (28) 766 ± 170 | | (26) 643 ± 121 | (27) 601 ± 145 | (27) 624 ± 121 | (27) 1061 ± 224 | (27) 557 ± 89 | (27) 925 ± 180 |
| Early CI | | | | | | | | |
| Baseline | (29) 1105 ± 249 | (30) 501 ± 136 | (30) 856 ± 226 | (30) 969 ± 253 | (30) 1124 ± 234 | (30) 1148 ± 241 | (30) 903 ± 176 | (30) 1215 ± 265 |
| Month 12 | (29) 650 ± 138 | (30) 445± | (30) 737 ± 182 | (30) 792 ± 184 | (30) 869 ± 199 | (30) 1053 ± 256 | (30) 609 ± 136 | (30) 1040 ± 227 |
| p value | 0.060 | | 0.408 | 0.421 | 0.088 | 0.936 | 0.006 | 0.0692 |
| Late Placebo | | | | | | | | |
| Baseline | (30) 851 ± 217 | (29) 626 ± 149 | (29) 903 ± 269 | (29) 682 ± 200 | (30) 1056 ± 213 | (29) 1031 ± 247 | (29) 793 ± 183 | (29) 1042 ± 228 |
| Month 12 | (29) 1025± | | (29) 967 ± 203 | (29) 889± | (30) 1020 ± 155 | (28) 1352 ± 261 | (30) 1060± | (29) 1154 ± 217 |
| Late CI | | | | | | | | |
| Baseline | (16) 877 ± 252 | (15) 856 ± 328 | (16) 579 ± 255 | (16) 644 ± 227 | (16) 727 ± 189 | (16) 615 ± 258 | (16) 559 ± 199 | (16) 601 ± 174 |
| Month 12 | (16) 743 ± 206 | (16) 564± | (16) 1097 ± 364 | (16) 565 ± 97 | (16) 693 ± 188 | (16) 739 ± 185 | (16) 559 ± 123 | (16) 937 ± 280 |
| p value | 0.265 | | 0.874 | 0.764 | 0.980 | | | 0.479 |

TABLE 6

IFNγ Production by SSc PBMC Cultured with Bovine α2(I) CB Peptides at Baseline and 12 Months α2 CB Peptides

| | (n) CB Mix | (n) CB4 | (n) CB2 | (n) CB3 | (n) CB 3–5 |
|---|---|---|---|---|---|
| Total Placebo | | | | | |
| Baseline | (58) 886 ± 165 | (56) 854 ± 147 | (58) 584 ± 117 | (56) 774 ± 137 | (58) 795 ± 146 |
| Month 12 | (57) 902 ± 135 | (56) 801 ± 110 | (57) 647 ± 109 | (55) 873 ± 128 | (57) 872 ± 121 |
| Total CI | | | | | |
| Baseline | (45) 1006 ± 187 | (46) 842 ± 156 | (46) 551 ± 110 | (45) 1022 ± 196 | (46) 830 ± 172 |
| Month 12 | (45) 619 ± 102 | (45) 690 ± 130 | (46) 424 ± 69 | (45) 805 ± 147 | (46) 696 ± 111 |
| p value | 0.0185 | 0.300 | 0.139 | 0.440 | 0.372 |
| Early Placebo | | | | | |
| Baseline | (28) 763 ± 228 | (26) 581 ± 161 | (28) 558 ± 194 | (26) 556 ± 157 | (28) 711 ± 222 |
| Month 12 | (28) 817 ± 76 | (27) 643 ± 101 | (27) 496 ± 101 | (27) 776 ± 153 | (27) 739 ± 142 |
| Early CI | | | | | |
| Baseline | (29) 1105 ± 249 | (30) 1008 ± 227 | (30) 489 ± 110 | (30) 1290 ± 276 | (30) 1022 ± 245 |
| Month 12 | (29) 606 ± 126 | (29) 669 ± 176 | (30) 443 ± 94 | (29) 879 ± 205 | (30) 761 ± 158 |
| p value | 0.011 | 0.078 | 0.153 | 0.083 | 0.087 |
| Late Placebo | | | | | |
| Baseline | (30) 1001 ± 241 | (30) 1091 ± 230 | (30) 609 ± 138 | (30) 962 ± 213 | (30) 874 ± 194 |
| Month 12 | (29) 984 ± 206 | (29) 948 ± 189 | (30) 783 ± 184 | (28) 966 ± 205 | (30) 991 ± 189 |
| Late CI | | | | | |
| Baseline | (16) 827 ± 275 | (16) 532 ± 117 | (16) 667 ± 244 | (15) 486 ± 120 | (16) 470 ± 159 |
| Month 12 | (16) 644 ± 178 | (16) 730 ± 187 | (16) 388 ± 96 | (16) 673 ± 189 | (16) 578 ± 127 |
| p value | 0.507 | 0.687 | 0.475 | 0.359 | 0.661 |

TABLE 7

IL-10 Production by SSc PBMC at Baseline and 12 Months

|  | (n) PBS | (n) PHA | (n) Cand | (n) BCI | (n) Hα1(I) | (n) Hα2(I) |
|---|---|---|---|---|---|---|
| Total Placebo |  |  |  |  |  |  |
| Baseline | (65) 382 ± 93 | (64) 1500 ± 177 | (52) 168 ± 40 | (64) 537 ± 83 | (65) 827 ± 99 | (65) 641 ± 85 |
| Month 12 | (65) 277 ± 36 | (63) 1131 ± 135 | (64) 195 ± 23 | (65) 240 ± 25 | (61) 579 ± 85 | (61) 433 ± 47 |
| Total CI |  |  |  |  |  |  |
| Baseline | (51) 247 ± 48 | (51) 1263 ± 219 | (41) 118 ± 24 | (51) 398 ± 91 | (49) 604 ± 87 | (49) 425 ± 71 |
| Month 12 | (51) 293 ± 43 | (51) 1438 ± 219 | (50) 260 ± 50 | (51) 256 ± 37 | (49) 536 ± 66 | (49) 466 ± 66 |
| p value | 0.565 | 0.172 | 0.778 | 0.234 | 0.093 | 0.052 |
| Early Placebo |  |  |  |  |  |  |
| Baseline | (34) 308 ± 77 | (33) 1656 ± 258 | (28) 205 ± 69 | (33) 577 ± 128 | (34) 984 ± 155 | (34) 700 ± 135 |
| Month 12 | (34) 328 ± 59 | (32) 1180 ± 189 | (33) 212 ± 33 | (34) 264 ± 38 | (32) 578 ± 109 | (32) 463 ± 71 |
| Early CI |  |  |  |  |  |  |
| Baseline | (34) 271 ± 64 | (34) 1314 ± 264 | (27) 136 ± 34 | (34) 478 ± 127 | (33) 665 ± 112 | (33) 462 ± 96 |
| Month 12 | (34) 281 ± 43 | (34) 1290 ± 119 | (33) 235 ± 57 | (34) 239 ± 42 | (33) 495 ± 78 | (33) 400 ± 59 |
| p value | 0.922 | 0.541 | 0.966 | 0.826 | 0.314 | 0.376 |
| Late Placebo |  |  |  |  |  |  |
| Baseline | (31) 463 ± 175 | (31) 1334 ± 242 | (24) 125 ± 30 | (31) 493 ± 106 | (31) 655 ± 113 | (31) 577 ± 99 |
| Month 12 | (31) 220 ± 37 | (31) 1082 ± 194 | (31) 177 ± 32 | (31) 213 ± 32 | (29) 581 ± 136 | (29) 400 ± 62 |
| Late CI |  |  |  |  |  |  |
| Baseline | 75(17) 199 ± 64 | (17) 1161 ± 403 | (14) 83 ± 24 | (17) 239 ± 96 | (16) 479 ± 131 | (16) 348 ± 90 |
| Month 12 | (17) 319 ± 98 | (17) 1734 ± 476 | (17) 310 ± 100 | (17) 289 ± 75 | (16) 621 ± 123 | (16) 602 ± 159 |
| p value | 0.457 | 0.185 | 0.868 | 0.070 | 0.122 | 0.039 |

TABLE 8

IL-10 Production by SSc PBMC Cultured with Bovine α1(I) CB Peptides at Baseline and 12 months

| | α1(I) CB Peptides | | | | | | | |
|---|---|---|---|---|---|---|---|---|
|  | (n) a1 CB Mix | (n) CB2 | (n) CB4 | (n)CB5 | (n) CB8 | (n) CB3 | (n) CB7 | (n) CB6 |
| Total Placebo |  |  |  |  |  |  |  |  |
| Baseline | (64) 714 ± 97 | (62) 297 ± 53 | (62) 785 ± 180 | 10 (62) 426 ± 61 | (64) 881 ± 106 | (63) 696 ± 98 | (63) 476 ± 61 | (62) 754 ± 99 |
| Month 12 | (64) 491 ± 55 | (62) 341 ± 47 | (62) 519 ± 61 | (63) 425 ± 52 | (64) 619 ± 67 | (62) 713 ± 79 | (64) 461 ± 52 | (63) 746 ± 89 |
| Total CI |  |  |  |  |  |  |  |  |
| Baseline | (50) 608 ± 108 | (49) 244 ± 44 | (50) 727 ± 208 | (49) 357 ± 61 | (49) 656 ± 98 | (50) 633 ± 103 | (49) 377 ± 63 | (49) 867 ± 128 |
| Month 12 | (50) 515 ± 86 | (50) 362 ± 53 | (50) 852 ± 176 | (50) 452 ± 58 | (51) 714 ± 88 | (50) 810 ± 97 | (51) 531 ± 55 | (50) 750 ± 88 |
| p value | 0.508 | 0.505 | 0.180 | 0.360 | 0.129 | 0.159 | 0.046 | 0.638 |
| Early Placebo |  |  |  |  |  |  |  |  |
| Baseline | (33) 858 ± 163 | (32) 361 ± 94 | (32) 1134 ± 307 | (32) 502 ± 102 | (33) 1069 ± 177 | (33) 904 ± 173 | (33) 562 ± 106 | (32) 986 ± 161 |
| Month 12 | (34) 572 ± 92 | (33) 392 ± 78 | (32) 503 ± 83 | (33) 495 ± 80 | (33) 701 ± 112 | (33) 795 ± 116 | (33) 560 ± 83 | (33) 768 ± 114 |
| Early CI |  |  |  |  |  |  |  |  |
| Baseline | (33) 1699 ± 157 | (33) 244 ± 45 | (33) 756 ± 241 | (33) 366 ± 76 | (33) 67 ± 133 | (33) 712 ± 149 | (33) 430 ± 87 | (33) 863 ± 150 |
| Month 12 | (33) 413 ± 61 | (34) 351 ± 71 | (34) 789 ± 200 | (34) 381 ± 53 | (34) 615 ± 74 | (34) 799 ± 118 | (34) 480 ± 57 | (34) 695 ± 82 |
| p value | 0.969 | 0.957 | 0.082 | 0.943 | 0.126 | 0.362 | 0.568 | 0.753 |
| Late Placebo |  |  |  |  |  |  |  |  |
| Baseline | (31) 560 ± 95 | (30) 228 ± 43 | (30) 413 ± 153 | (30) 344 ± 63 | (31) 681 ± 102 | (30) 467 ± 57 | (30) 382 ± 51 | (30) 505 ± 94 |
| Month 12 | (30) 399 ± 50 | (29) 283 ± 46 | (30) 537 ± 92 | (30) 347 ± 63 | (31) 532 ± 66 | (29) 621 ± 104 | (31) 356 ± 56 | (30) 721 ± 140 |

TABLE 8-continued

IL-10 Production by SSc PBMC Cultured with Bovine α1(I) CB Peptides at Baseline and 12 months

| | α1(I) CB Peptides | | | | | | | |
|---|---|---|---|---|---|---|---|---|
| | (n) a1 CB Mix | (n) CB2 | (n) CB4 | (n) CB5 | (n) CB8 | (n) CB3 | (n) CB7 | (n) CB6 |
| Late CI | | | | | | | | |
| Baseline | (17) 431 ± 80 | (16) 224 ± 102 | (17) 671 ± 403 | (16) 340 ± 106 | (16) 633 ± 126 | (17) 479 ± 79 | (16) 269 ± 70 | (16) 880 ± 246 |
| Month 12 | (17) 714 ± 219 | (16) 386 ± 73 | (16) 987 ± 357 | (16) 605 ± 138 | (17) 911 ± 213 | (16) 833 ± 174 | (17) 633 ± 119 | (16) 866 ± 214 |
| p value | 0.232 | 0.293 | 0.545 | 0.141 | 0.530 | 0.188 | 0.010 | 0.304 |

TABLE 9

IL-10 Production by SSc PBMC Cultured with α2 (I) CP Peptides at Baseline and 12 Months

| | α2 (1) CB Peptides | | | | |
|---|---|---|---|---|---|
| | (n) CB Mix | (n) CB4 | (n) CB2 | (n) CB3 | (n) CB3–5 |
| Total Placebo | | | | | |
| Baseline | (64) 700 ± 87 | (62) 910 ± 114 | (64) 331 ± 57 | (63) 904 ± 137 | (64) 866 ± 133 |
| Month 12 | (64) 466 ± 49 | (61) 596 ± 68 | (65) 349 ± 42 | (61) 660 ± 77 | (65) 612 ± 73 |
| Total CI | | | | | |
| Baseline | (50) 719 ± 114 | (50) 725 ± 108 | (50) 225 ± 33 | (48) 713 ± 106 | (50) 840 ± 121 |
| Month 12 | (50) 510 ± 64 | (49) 583 ± 75 | (50) 317 ± 35 | (50) 707 ± 83 | (49) 657 ± 92 |
| p value | 0.292 | 0.356 | 0.772 | 0.283 | 0.909 |
| Early Placebo | | | | | |
| Baseline | (33) 804 ± 147 | (31) 1082 ± 179 | (33) 422 ± 102 | (32) 1107 ± 244 | (33) 1044 ± 230 |
| Month 12 | (34) 502 ± 79 | (32) 684 ± 118 | (34) 386 ± 63 | (32) 772 ± 130 | (34) 708 ± 117 |
| Early CI | | | | | |
| Baseline | (33) 844 ± 164 | (33) 748 ± 149 | (33) 216 ± 34 | (33) 754 ± 132 | (33) 905 ± 151 |
| Month 12 | (33) 475 ± 61 | (33) 549 ± 85 | (34) 312 ± 42 | (33) 649 ± 87 | (33) 670 ± 115 |
| p value | 0.865 | 0.367 | 0.837 | 0.711 | 0.600 |
| Late Placebo | | | | | |
| Baseline | (31) 589 ± 87 | (31) 737 ± 135 | (31) 234 ± 41 | (31) 694 ± 111 | (31) 676 ± 119 |
| Month 12 | (30) 425 ± 53 | (29) 500 ± 58 | (31) 308 ± 53 | (29) 536 ± 73 | (31) 506 ± 80 |
| Late CI | | | | | |
| Baseline | (17) 478 ± 85 | (17) 681 ± 141 | (17) 241 ± 73 | (15) 623 ± 179 | (17) 715 ± 205 |
| Month 12 | (17) 578 ± 147 | (16) 654 ± 152 | (16) 326 ± 67 | (17) 819 ± 175 | (16) 632 ± 155 |
| p value | 0.069 | 0.610 | 0.955 | 0.211 | 0.501 |

What is claimed is:

1. A method for treating a scleroderma (SSc) in a patient, comprising orally administering to the patient one or more collagen fragments, said collagen fragments selected from the group consisting of: α1(I) CB1, CB2, CB3, CB4, CB5, CB6, CB7, CB8 and α2(I) CB1, CB2, CB3, CB4 and CB5.

2. The method of claim 1, wherein said patient has been suffering from said scleroderma (SSc) for at least 3 years.

3. The method of claim 1, wherein said collagen is derived from human or an animal species other than human.

4. The method of claim 1, wherein said collagen fragment is orally administered to said patient at about 500 μg/day.

5. The method of claim 4, wherein the patient is treated for about 12 months.

6. The method of claim 1, wherein the oral administration of said collagen fragment induces tolerance in said patient.

* * * * *